United States Patent [19]

Ochs et al.

[11] 4,043,325

[45] Aug. 23, 1977

[54] CERVICAL COLLARS

[76] Inventors: David J. Ochs, 707 W. Magnolia; James D. Behrens, 4101 W. Lakeview Drive; John H. Stevens, 3425 Arapahoe Drive, all of Fort Collins, Colo. 80521

[21] Appl. No.: 722,717

[22] Filed: Sept. 13, 1976

[51] Int. Cl.$^2$ ............................................. A61H 1/02
[52] U.S. Cl. .................................... 128/75; 128/87 B
[58] Field of Search ................ 128/75, 87 B, DIG. 23

[56] References Cited

U.S. PATENT DOCUMENTS

| | | | |
|---|---|---|---|
| 2,806,471 | 9/1957 | Breese | 128/87 B |
| 3,374,785 | 3/1968 | Gaylord, Jr. | 128/75 |
| 3,512,523 | 5/1970 | Barnett | 128/75 |

OTHER PUBLICATIONS

Zimmer Mfg. Catalogue, "Cervacollar", May 12, 1966.

*Primary Examiner*—John D. Yasko
*Attorney, Agent, or Firm*—Hugh H. Drake

[57] ABSTRACT

A strip of resistantly-resilient material is of a length such that its end portions overlap when encircled around a wearer's neck as a cervical collar. An intermediate lengthwise portion of the strip, positionable beneath the chin, is of increased width. A combination of fastener-part pairs, on different interior and exterior surfaces of end portions of the strip, serve to releasably fasten the collar in place. First and second pairs of straps are secured to the strip in the vicinity of opposite ends of the enlarged intermediate portion and extend around the head of the wearer to a location where the straps are detachably secured.

26 Claims, 6 Drawing Figures

U.S. Patent   Aug. 23, 1977   Sheet 1 of 2   4,043,325
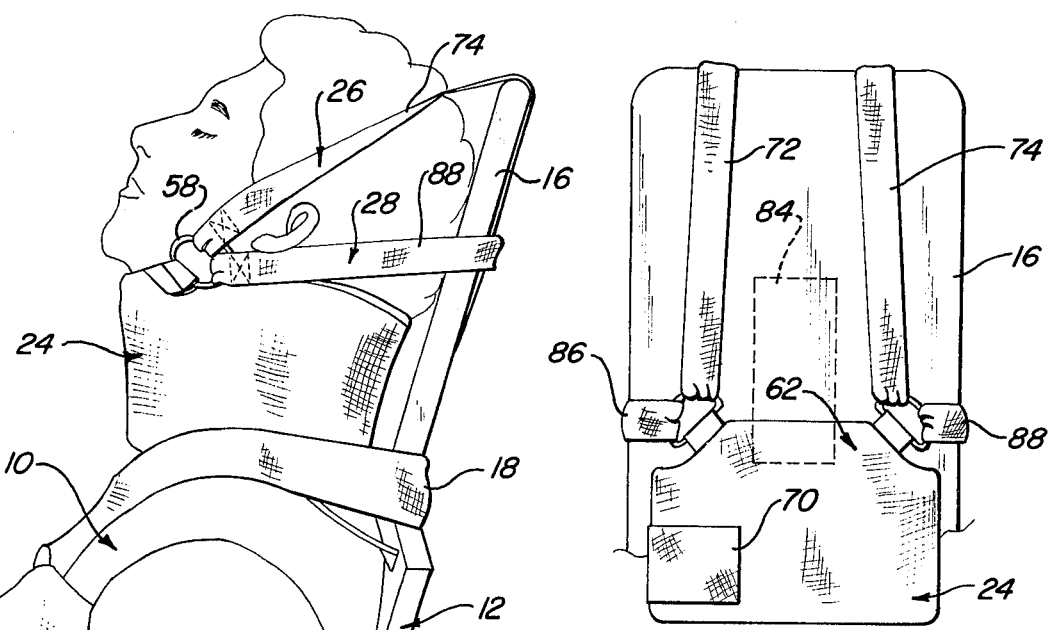
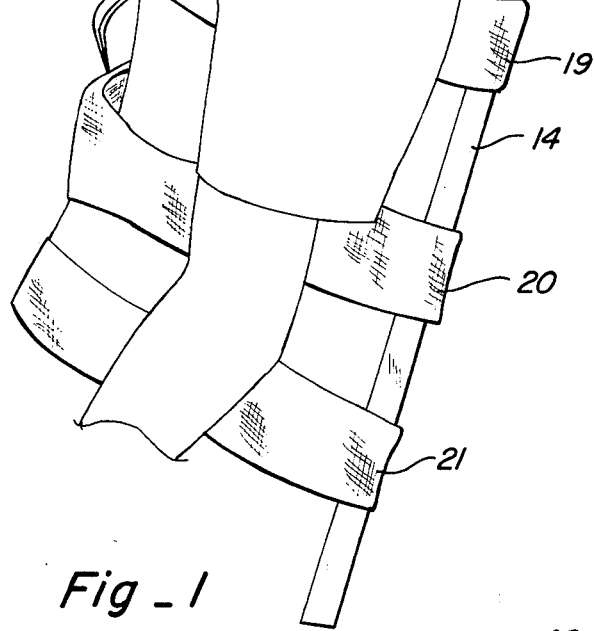
Fig_1
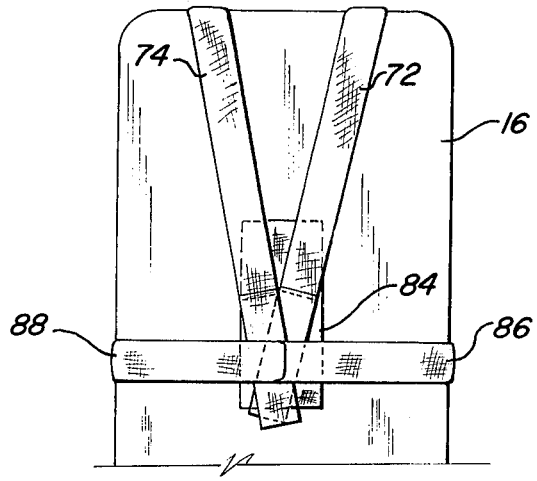
Fig_2
Fig_3
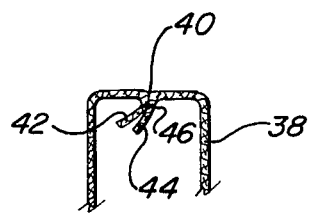
Fig_6

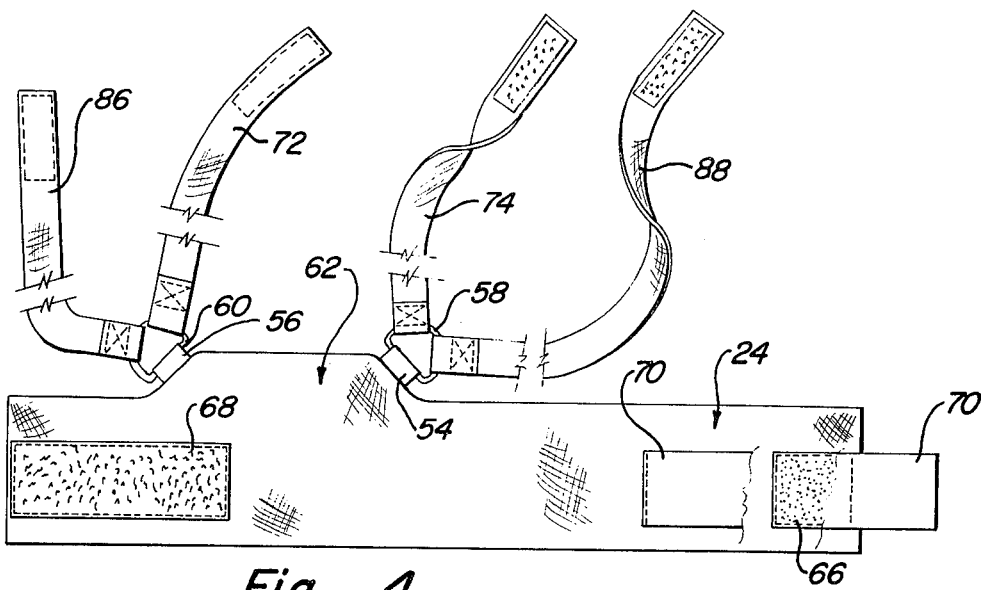
Fig _ 4
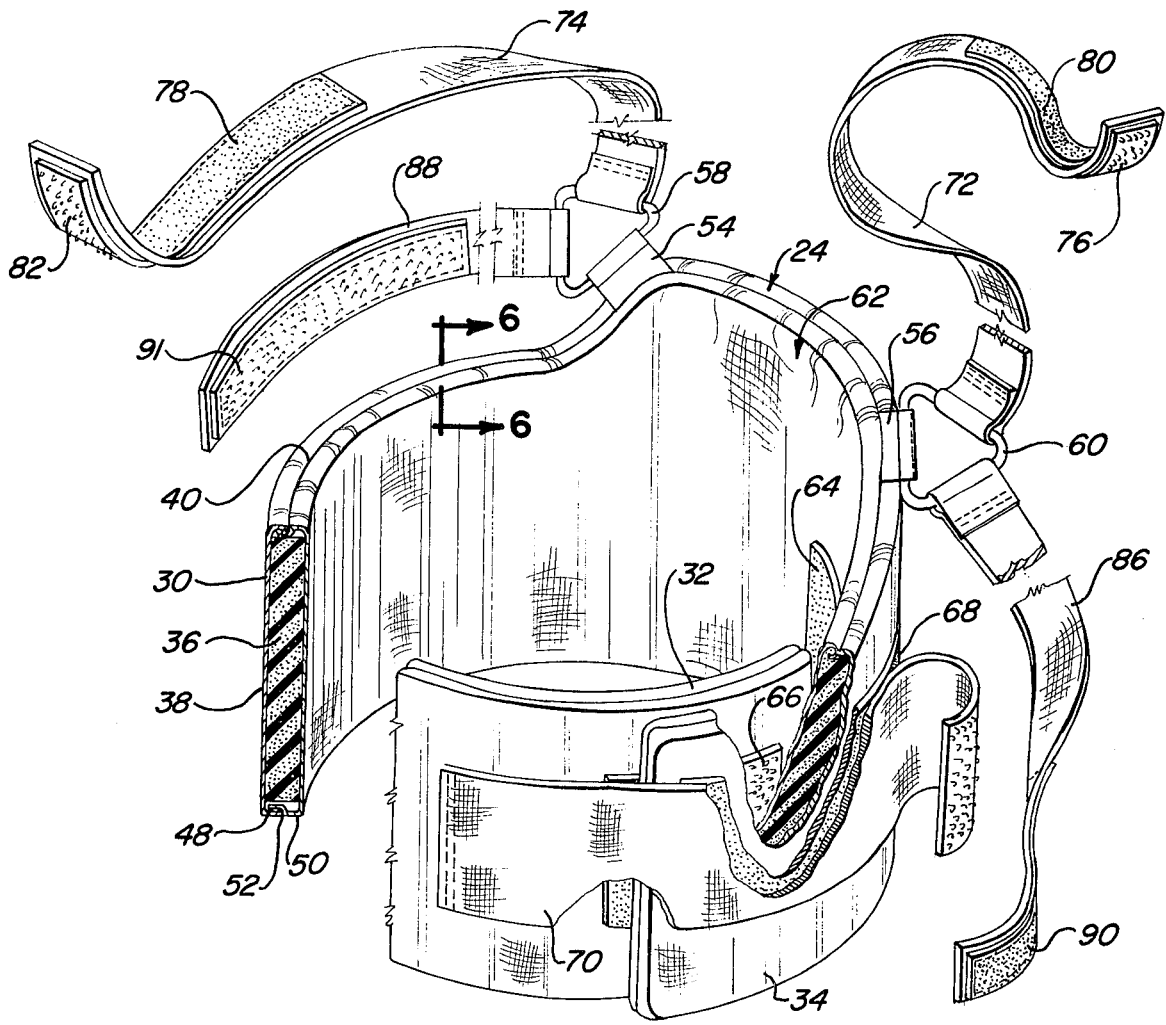
Fig _ 5

CERVICAL COLLARS

The present invention pertains to cervical collars. More particularly, it relates to a cervical collar of the detachable type appropriate for use in connection with the extrication and movement of a victim at least suspected to have suffered back and neck injury.

It is recognized in the field of emergency medical assistance that a person, at all suspected of having suffered back or neck injury, should not be moved until the back and neck regions have been immobilized. Otherwise, severe and sometimes permanent further injury may be induced in the process of moving and transporting the victim. Consequently, the usual approach has been to strap the upper torso of the victim to a rigid structure such as a backboard or a stretcher. The victim's neck is encased within a detachable band of firm but somewhat resilient material. In addition, a cup-like member is engaged over the chin of the victim and secured by straps around a rigid structure at the rear of the victim. The latter is preferably so fastened as to effect a slight degree of traction on the victim's neck.

It is a general object of the present invention to provide a cervical collar which is an improvement as compared with those of the kind discussed above.

Another object of the present invention is to provide a cervical collar which includes a new and improved arrangement for fastening the collar around the neck of the wearer.

A further object of the present invention is to provide a cervical collar which effects improved immobilization of the cervical region of the wearer.

Still another object of the present invention is to provide a new and improved cervical collar which eliminates the need for also utilizing a separate chin restraint.

A cervical collar constructed in accordance with the present invention includes a strip of resistantly-resilient material having a length sufficient for its respective end portions to overlap when the strip encircles the wearer's neck; its nominal width approximates at least the minimum distance between the mandible and the clavicle of the wearer. Also included are means for releasably fastening the end portions together in overlapping relationship with the strip disposed around the neck. One principal feature is the formmation of the strip to have an intermediate lengthwise portion of increased width, greater than the distance in normal posture between the underside of the chin and approximately the upper end of sternum, positionable beneath the chin. Another principle feature involves first and second fastener parts included in the fastening means; the first fastener part is disposed on the interior surface of the strip near one end thereof and the second fastener part, matable with the first, is disposed on the exterior surface of the strip near the other end thereof. A related feature includes the use of a third fastener part disposed on the exterior surface of the strip near the one end and opposite the first fastener part together with a fourth fastener part, matable with the third, secured on the exterior surface of the strip inwardly of the second fastener part from the other end. Incorporating still another principal feature, a first strap is secured at one end to the collar in the vicinity of one mandibular joint when the strip is disposed around the neck. A second strap is secured at one end of the collar in the vicinity of the other mandibular joint. The straps have a combined length at least sufficient to encircle the head. On the other ends of the straps are means for detachably securing them in encircling relationship to the head.

The features of the present invention which are believed to be novel are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 1 is a fragmentary side-elevational view illustrating a person immobilized by emergency medical apparatus which includes a cervical collar;

FIG. 2 is a fragmentary front-elevational view of the apparatus of FIG. 1 but with the representation of the person omitted;

FIG. 3 is a fragmentary rear-elevational view of the apparatus shown in FIGS. 1 and 2;

FIG. 4 is an exterior view of the cervical collar removed from the assemblage of FIG. 1 and laid out in a generally flat configuration.

FIG. 5 is an enlarged perspective view of the collar of FIG. 4 conformed to its in-use configuration; and FIG. 6 is a fragmentary cross-sectional view taken along the line 6—6 in FIG. 5.

FIG. 1 illustrates a person or victim 10 in a position with his upper torso, cervical or neck region and head immobilized by restraints which secure the victim to a backboard 12. As shown, backboard 12 is of a conventional type which is constructed of a rigid sheet such as heavy plywood and includes a lower portion 14 of a width and length as to accommodate the backside of the upper torso of victim 10 placed thereagainst. Projecting integrally upward from portion 14 is a more narrow stub 16 of a height that preferably is somewhat wider than the width of the victim's head and of a length so as to extend above the head.

In this case, the upper torso is secured to main portion 14 of the backboard by means of a plurality of straps 18, 19, 20 and 21. While straps 18-21 may be arranged and secured in a variety of different manners, they preferably are constructed and combined as described in U.S. Pat. No. 3,889,669, granted June 17, 1975.

Encircling the neck region of victim 10 is a cervical collar 24. Binding collar 24 in this case to stub 16 are upper and lower strap assemblies 26 and 28 which extend from the collar respectively over or around to the rear side of stub 16. As discussed more fully hereinafter, strap assemblies 26 and 28 may be secured in position in several different ways. However, it is always desired that they somehow be affixed with relationship to a rigid object placed generally behind the victim. As already indicated, that might be a part of a stretcher instead of backboard 12. In the absence or unuseability of a conventional structure such as a backboard or stretcher, anyone seeking to attend the victim should seek to use anything else which is rigid and somehow can be fit into place. For example, that might include a book or briefcase placed behind the head, neck and shoulders, a plank or something taken from a nearby object such as a cooler top or a cabinet door.

Turning more specifically to collar 24 itself, it is formed to include a strip 30 of a resistantly-resilient material and of a length sufficient for its respective end portions 32 and 34 to overlap when the strip is encircled around the neck of victim 10. Strip 30 has a nominal width, such as the width of end portions 32 and 34, which approximates at least the minimum distance between the mandible and clavicle of the wearer. Of course, it is at least normally not feasible to maintain a supply of a plurality of collars having a large number of different nominal widths so as to be able to accommodate perfectly all victims that might be encountered; the width of strip 20 is selected so as to be slightly greater than the aforesaid minimum distance when applied to a majority of the victims to which the collar may be applied. This is for the purpose of inducing a modest degree of traction in the cervical region when the collar is placed on the neck.

Strip 30 preferably is composed of a core 36 of resistantly-resilient material. By the latter is meant that it exhibits resilience so as to return to its original shape after having been deformed or compressed, while at the same time it exhibits a high degree of firmness in resistance against such deformation or compression. That is, what might be termed the "squeeze" characteristic of core 36 is that it is more like a dry, dense felt than like a wet sponge. A preferred material is a one-half inch thick high-density unicellular form of synthetic rubber. The latter provides the added advantage of being non-absorbant to water.

As best shown in FIGS. 5 and 6, core 36 is encased within a flexible covering 38. Desirably, covering 38 is formed of a soft nylon so as to be flexible while at the same time being washable and waterproof. Covering 38 includes a lengthwise seam 40 formed with mutually-facing in-turned marginal edge portions 42 and 44 secured together as by sewing 46 beneath the exterior surface of the covering.

During fabrication, cover 38 may be formed from a suitably-shaped single piece of material so as to have only the one seam 40. As indicated in FIG. 5, the approach of the illustrated embodiment involves the formation of cover 38 from a mating pair of panels 48 and 50, so that another seam 52 exists along the bottom margin of the collar. During fabrication, the two panels are placed together in face-to-face relationship, and the longitudinal marginal-edge portions thereof, as well as the end margin of end portion 32 (which in use will lie at least near the wearer's neck, is sewed as indicated at 46. At the same time, webbing loops 54 and 56, to be discussed further, also are sewed in place while serving to couple respective D-rings 58 and 60 firmly to covering 38. The thus formed sleeve of covering 38 is then turned inside out so as to leave marginal edge portions 42 and 44 concealed and not in a position, when the ultimate collar is used, to chafe the neck of the wearer. Thereafter, the basic collar itself is completed by stuffing core 36 into the interior of covering 38. Finally, the panel end margins of end portion 34 are sewn together.

An intermediate lengthwise portion 62 of strip 30 is of increased width. That width is selected so as to be greater than the distance, in normal posture of victim 10, between the underside of the chin and approximately the upper end of the sternum when portion 62 is disposed beneath the chin. Thus, panels 48 and 50 as well as core 36 are shaped so as to result in the formation of enlarged-width portion 62. When collar 24 is properly placed around the neck of the wearer, portion 62 induces a degree of additional traction or hyperextension in the cervical region of the wearer. In addition, portion 62 insures the maintenance of an orientation of the chin of the wearer so as to assist in the maintaining of clearance of this airway.

Included in collar 24 are means for releasably fastening end portions 32 and 34 in overlapping relationship. A first fastener part 64 is disposed, as by sewing, on the interior surface of end portion 34 of strip 30. A second fastener part 66, matable with part 64, is disposed on the exterior surface of end portion 32 near the other end of strip 30. Collar 24 may be fastened around the neck of the wearer simply by overlapping end portion 34 on the outside of end portion 32 and securing parts 64 and 66 together. It will be observed that fastener parts 64 and 66 end up being at least substantially concealed when the collar is in place on the neck of the wearer. Thus, it is not feasible to use a buckle-type fastener for these parts. While a snap-fastener arrangement could be employed, it is preferred to utilize a self-cohering fastener of a kind permitting essentially infinite length adjustment. To that end, fastener parts 64 and 66 together preferably constitute what has become widely known as the Velcro fastener. This type of fastener features a first sheet of material, such as part 64, that presents a densely-compacted outwardly-facing plurality of minute loops. Its mate, part 66, presents a similarly-compacted outwardly-facing plurality of minute hooks. When the two parts are pressed together at any relative lengthwise position as between the two parts, a sufficient number of hooks engage the loops so that the two parts are firmly bound together. Yet, they may subsequently be detached simply by stripping one away from the other, the hooks having sufficient resilient conformity as to permit that function. This kind of fastener is especially attractive in that it permits an infinite adjustment of point of attachment and yet is only cohesive in that the two parts will bond to each other but do not readily interact with extraneous materials.

Preferably adding additional security to the fastening between end portion 32 and 34 are another pair of fastener parts which again preferably are at least in the nature of that of the described Velcro fasteners. A third fastener part 68 is disposed on the exterior surface of end portion 34 of strip 30 and a matable fourth fastener part 70 is secured on the exterior surface of end portion 32 of strip 30 inwardly along the strip from fastener part 66. After collar 24 has been placed on the neck and fastener parts 64 and 66 engaged, fastener part 70 is brought around and over fastener part 68 so as to complete an additional degree of fastening between end portions 32 and 34.

Strap assembly 26 includes a first strap 72 secured at one end to collar 24 in the vicinity of one end of intermediate portion 62 by means of a leg of D-ring 60 and loop 56. A second strap 74 is secured at one end to collar 24 in the vicinity of the other end of intermediate portion 62 by means of D-ring 58 and loop 54. Each of straps 72 and 74 have a combined length at least sufficient so as together to encircle the head of person or victim 10. Preferably, that combined length is sufficient so as also to encircle at least stub 16 when placed behind the head of victim 10.

The free ends of straps 72 and 74 are arranged so as to be detachably secured in a manner to encircle the head of victim 10. To this end, one side of the respective end portion of each of straps 72 and 74 includes a respective one of fastener parts 76 and 78. As between themselves, parts 76 and 78 are mutually matable so as enable the fastening of straps 72 and 74 together in a manner to encircle the head of the victim or wearer. Preferably and as already indicated, straps 72 and 74 encircle not only the head but also a rigid support, such as stub 16, placed behind the head of the wearer. Thus, fastener parts 76 and 78 permit fastening of the straps behind such an object. In the absence of a separate support, however, fastener parts 76 and 78 permit the respective straps to be fastened together firmly around and over the top of the head of the wearer. In any case, it is desired that straps 72 and 74 desirably are canted rearwardly and upwardly so as, when fastened, to effect a vertical stabilization of the cervical region of the wearer. A smooth orientation of straps 72 and 74 as so canted is facilitated by the shape of D-rings 58 and 60.

In order to permit a maximum in flexibility of adaptation and usage of straps 72 and 74, the free end portions thereof preferably also include respective and mutually-matable additional fastener parts 80 and 82 correspondingly secured to the free end portions of the straps on the sides thereof opposite fastener parts 76 and 78. At least in some situations, these assist in enabling the fastening of the free ends of straps 72 and 74 to any other fastener parts a portion of which may be available for such purpose anywhere else in the overall assembly. In addition, it is also contemplated to secure a fastener part 84 on the rear surface of stub 16 of the associated headboard 12 so as to be in a position behind the head of victim 10. Fastener part 84 preferably is of one Velcro gender or the like so as to be matable with one of the fastener parts on each free end portion of straps 72 and 74. Thus, and as best shown in FIGS. 2 and 3, straps 72 and 74 may be oriented so as to extend over the top of stub 16 and then have respective fastener parts on their free ends secured to matable fastener part 84. Depending upon the relative placement and gender of the different fastener parts, this may involve a need to incorporate a half-twist into one of straps 72 and 74; of course, such twist should be made at a place in the strap free of the victim.

In order to provide increased horizontal stabilization of the cervical region, collar 24 still further includes a third strap 86 secured at one end to the collar again in the vicinity of one end of intermediate portion 62 by means of D-ring 60 and loop 56. Similarly, a fourth strap 88 is secured at one end to collar 24 in the vicinity of the other end of portion 62 and by means of a leg of D-ring 58 and loop 54. Straps 86 and 88 also have a combined length at least sufficient to encircle the head of the wearer, and they include means for detachably affixing their other or free ends so as together to encircle at least the head of the wearer. Once more, it is desirable that the combined length of straps 86 and 88 be sufficient so as also to encircle a rigid support such as stub 16. The free end of strap 86 includes a first fastener part 90 matable with a second fastener part 91 disposed on the free end of strap 88. As before, fastener parts 90 and 91 preferably are of the Velcro type. When secured in place, it will be observed that straps 86 and 88 are disposed below straps 72 and 74.

Straps 72, 74, 86 and 88 are affixed or coupled to collar 24 at respective locations which in use of the collar are in the vicinity of the corresponding mandibular joints of the wearer. Related to those locations, as well as to the formation of enlarged portion 32, end portions 32 and 34 are of such different respective lengths as to dispose their mutual overlap on the side of the neck where enlarged portion 62 is positioned beneath the chin. This assures that fastener parts 64, 66, 68 and 70 are readily available to the attendant without interference from backboard 12 or the like.

In practical implimentation, the total length of a collar, proportioned as generally represented in FIG. 5, will be about 24 inches for adult users. The nominal width may be 4 inches with portion 62 having its width increased by approximately 1¼ inches. Upper straps 72 and 74 desirably are about 20 inches in length for use in conjunction with a standard short backboard. Similarly, lower straps 86 and 88 may have a length of about 14 inches. Desirably, the strap pairs are mutually color coded so as to assist the attendant in quickly making certain that he has the correct straps properly oriented and connected.

It will be appreciated that the disclosed collar represents significant improvement in several respects. The raised lip of intermediate portion 62 assists in establishing the desired traction as well as in maintaining airway clearance. The mode of fastening the collar about the neck is not only secure but extremely easy of utilization in application. The integrally associated straps permit both horizontal and vertical stabilization of the cervical region without the need for accessory devices. Yet, the entire assemblage is comparatively easy and economical of manufacture. Also, it is capable of including such desirable characteristics as continued performance even when wet and complete washability for purposes of reuse.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A cervical collar comprising:
a strip of resistantly-resilient material having a length sufficient for its respective end portions to overlap when said strip is installed around the neck of the wearer, the nominal width of said strip approximating at least the minimum distance between the mandible and the clavicle of the wearer, and said material including a high-density unicellular foam encased within a flexible covering with said covering including at least one lengthwise seam formed with mutually-facing in-turned marginal edge portions secured together beneath the exterior surface of said covering;
an intermediate lengthwise portion of said strip having an increased width, greater than the distance in normal posture between the underside of the chin and approximately the upper end of the sternum of the wearer, positionable beneath said chin;
and means releasably fastening said end portions together in overlapping relationship with said strip disposed around the neck of said wearer and said increased-width portion positioned between said chin.

2. A cervical collar comprising:
a strip of resistantly-resilient material having a length sufficient for its respective end portions to overlap when said strip is encircled around the neck of a wearer, the nominal width of said strip approximately at least the minimum distance between the mandible and the clavicle of the wearer;
an intermediate lengthwise portion of said strip having an increased width, greater than the distance in normal posture between the underside of the chin and approximately the upper end of the sternum of the wearer, postionable beneath said chin;

means for releasably fastening said end portions together in overlapping relationship with said strip disposed around the neck of said wearer and said increased-width portion positioned beneath said chin;

and said end portions being of such respective different lengths, relative to said intermediate portion, that said fastening means is located on the side of said neck when the center of said intermediate portion is positioned beneath said chin.

3. A cervical collar comprising:

a strip of resistantly-resilient material having a length sufficient for its respective end portions to overlap when said strip is encircled around the neck of a wearer, the nominal width of said strip approximating at least the minimum distance between the mandible and the clavicle of said wearer;

an intermediate lengthwise portion of said strip having an increased width, greater than the distance in normal posture between the underside of the chin and approximately the upper end of the sternum of the wearer, positionable beneath said chin;

means for releasably fastening said end portions together in overlapping relationship with said strip disposed around the neck of said wearer and said increased-width portion positioned beneath said chin;

and said fastening means including a first fastener part disposed on the interior surface of said strip near one end thereof, a second fastener part, matable with the first, disposed on the exterior surface of said strip near the other end thereof, a third fastener part disposed on the exterior surface of said strip near said one end and opposite said first fastener part and a fourth fastener part, matable with the third, secured on the exterior surface of said strip inwardly of said second fastener part from said other end.

4. A cervical collar comprising:

a strip of resistantly-resilient material having a length sufficient for its respective end portions to overlap when said strip is encircled around the neck of a wearer, the nominal width of said strip approximating at least the minimum distance between the mandible and the clavicle of said wearer;

an intermediate lengthwise portion of said strip having an increased width, greater than the distance in normal posture between underside of the chin and approximately the upper end of the sternum of the wearer, positionable beneath said chin;

means for releasable fastening said end portions together in overlapping relationship with said strip disposed around the neck of said wearer and said increased-width portion positioned beneath said chin;

a first strap secured at one end of said collar in the vicinity of one end of said intermediate portion;

a second strap secured at one end to said collar in the vicinity of the other end of said intermediate portion;

said straps having a combined length at least sufficient to encircle the head of said wearer;

and means for detachably securing the other ends of said straps so as together to encircle the head of said wearer.

5. A collar as defined in claim 4 which further includes:

a third strap secured at one end to said collar in the vicinity of said one end of said intermediate portion;

a fourth strap secured at one end to said collar in the vicinity of said other end of said intermediate portion;

said third and fourth straps having a combined length at least sufficient to encircle the head of the wearer;

and means for detachably affixing the other ends of said third and fourth straps so as together to encircle the head of said wearer.

6. A collar as defined in claim 5 in which said first and second straps are disposed generally above said third and fourth straps, and in which the combined length of said first and second straps also is sufficient to enable a rearward and upward canting thereof so as to effect vertical stabilization of the cervical region of said wearer.

7. A collar as defined in claim 6 in which the combined length of said third and fourth straps is sufficient to enable horizontal stabilization of said cervical region.

8. A collar as defined in claim 5 in which said securing and affixing means are so disposed as to enable attaching together of all of said other ends of said straps generally behind the head of said wearer.

9. A collar as defined in claim 4 combined with a rigid support sized to be positioned behind the cervical region of said wearer, said securing means including a first fastener part on each of said other ends of said straps, and a second fastener part, matable with the first fastener part on each of said other ends, being disposed on the surface of said support in a position behind the head of said wearer.

10. A collar as defined in claim 4 in which said material includes a covering having at least one lengthwise seam formed with mutually-facing in-turned marginal edge portions secured together beneath the exterior surface of said covering, and in which said one ends of said straps are secured to said collar in common with the securement of said edge portions.

11. A cervical collar comprising:

a strip of resistantly-resilient material having a length sufficient for its respective end portions to overlap when said strip is encircled around the neck of a wearer, the nominal width of said strip approximating at least the minimum distance between the mandible and the clavicle of said wearer;

and means for releasably fastening said end portions together in overlapping relationship with said strip disposed around the neck of said wearer, said fastening means including a first fastener part disposed on the interior surface of said strip near one end thereof and a second fastener part, matable with the first, disposed on the exterior surface of said strip near the other end thereof, said fastening means further including a third fastener part disposed on the exterior surface of said strip near said one end and opposite said first fastener part and a fourth fastener part, matable with the third, disposed on the exterior surface of said strip inwardly of said second fastener part from said other end.

12. A cervical collar comprising:

a strip of resistantly-resilient material having a length sufficient for its respective end portions to overlap when said strip is encircled around the neck of a wearer, the nominal width of said strip approximating at least the minimum distance between the mandible and the clavicle of the wearer;

means for releasably fastening said end portions together in overlapping relationship with said strip disposed around the neck of said wearer, said fastening means including a first fastener part disposed on the interior surface of said strip near one end thereof and a second fastener part, matable with the first, disposed on the exterior surface of said strip near the other end thereof;

a first strap secured at one end to said collar in the vicinity of one mandibular joint when said strip is disposed around the neck of said wearer;

a second strap secured at one end to said collar in the vicinity of the other mandibular joint when said strip is so disposed;

said straps having a combined length at least sufficient to encircle the head of said wearer;

and means for detachably securing the other ends of said straps so as together to encircle the head of said wearer.

13. A collar as defined in claim 12 which further includes:

a third strap secured at one end in the vicinity of said one end of said first strap;

a fourth strap secured at one end in the vicinity of said one end of said second strap;

said third and fourth straps having a combined length at least sufficient to encircle the head of the wearer;

and means for detachably affixing the other ends of said third and fourth straps so as together to encircle the head of said wearer.

14. A collar as defined in claim 13 in which said first and second straps are disposed generally above said third and fourth straps, and in which the combined length of said first and second straps also is sufficient to enable a rearward and upward canting thereof so as to effect vertical stabilization of the cervical region of said wearer.

15. A collar as defined in claim 14 in which the combined length of said third and fourth straps is sufficient to enable horizontal stabilization of said cervical region.

16. A collar as defined in claim 13 in which said securing and affixing means are so disposed as to enable attaching together of all of said other ends of said straps generally behind the head of said wearer.

17. A collar as defined in claim 12 combined with a rigid support sized to be positioned behind the cervical region of said wearer, said securing means including a first fastener part on each of said other ends of said straps, and a second fastener part, matable with the first fastener part on each of said other ends, being disposed on the surface of said support in a position behind the head of said wearer.

18. A collar as defined in claim 12 in which said material includes a covering having at least one lengthwise seam formed with mutually-facing in-turned marginal edge portions secured together beneath the exterior surface of said covering, and in which said one ends of said straps are secured to said collar in common with the securement of said edge portions.

19. A cervical collar comprising:

a strip of resistantly-resilient material having a length sufficient for its respective end portions to overlap when said strip is encircled around the neck of a wearer, the nominal width of said strap approximating at least the minimum distance between the mandible and the clavicle of said wearer;

means for releasably fastening said end portions together in overlapping relationship with said strip disposed around the neck of said wearer;

a first strap secured at one end to said collar in the vicinity of one mandibular joint when said strip is disposed around the neck of said wearer;

a second strap secured at one end to said collar in the vicinity of the other mandibular joint when said strip is so disposed;

said straps having a combined length at least sufficient to encircle the head of said wearer;

and means for detachably securing the other ends of said straps so as together to encircle the heat of said wearer.

20. A collar as defined in claim 19 which further includes:

a third strap secured at one end in the vicinity of said one end of said first strap;

a fourth strap secured at one end in the vicinity of said one end of said second strap;

said third and fourth straps having a combined length at least sufficient to encircle the head of the wearer;

and means for detachably affixing the other ends of said third and fourth straps so as together to encircle the head of said wearer.

21. A collar as defined in claim 20 in which said first and second straps are disposed generally above said third and fourth straps, and in which the combined length of said first and second straps also is sufficient to enable a rearward and upward canting thereof so as to effect vertical stabilization of the cervical region of said wearer.

22. A collar as defined in claim 21 in which the combined length of said third and fourth straps is sufficient to enable horizontal stabilization of said cervical region.

23. A collar as defined in claim 20 in which said securing and affixing means are so disposed as to enable attaching together of all of said other ends of said straps generally behind the head of said wearer.

24. A collar as defined in claim 19 combined with a rigid support sized to be positioned behind the cervical region of said wearer, said securing means including a first fastener part on each of said other ends of said straps, and a second fastener part, matable with the first fastener part on each of said other ends, being disposed on the surface of said support in a position behind the head of said wearer.

25. A collar as defined in claim 19 in which said end portions are of such respective different lengths, relative to said straps, that said fastening means is located on the side of said neck when said strip is so disposed.

26. A collar as defined in claim 19 in which said material includes a covering having at least one lengthwise seam formed with mutually-facing in-turned marginal edge portions secured together beneath the exterior surface of said covering, and in which said one ends of said straps are secured to said collar in common with the securement of said edge portions.

* * * * *